United States Patent [19]

Furukawa et al.

[11] 4,355,040
[45] * Oct. 19, 1982

[54] HYPOTENSIVE IMIDAZOLE-5-ACETIC ACID DERIVATIVES

[75] Inventors: Yoshiyasu Furukawa, Toyonaka; Shoji Kishimoto, Takarazuka; Kohei Nishikawa, Kyoto, all of Japan

[73] Assignee: Takeda Chemical Industries, Ltd., Osaka, Japan

[*] Notice: The portion of the term of this patent subsequent to Jul. 20, 1999, has been disclaimed.

[21] Appl. No.: 204,357

[22] Filed: Nov. 5, 1980

[30] Foreign Application Priority Data

Nov. 12, 1979 [JP] Japan .................. 54-146728

[51] Int. Cl.³ .................. A61K 31/415; C07D 233/68
[52] U.S. Cl. .................. 424/273 R; 548/336; 548/337; 548/342
[58] Field of Search .................. 548/337; 424/273 R

[56] References Cited

U.S. PATENT DOCUMENTS 4,207,324  6/1980  Matsumura et al. ............ 548/337 X

FOREIGN PATENT DOCUMENTS 1535566  12/1978  United Kingdom .

OTHER PUBLICATIONS

Karppanen, Agents and Actions 9:84–85 (1979).
Maxwell, M. (Editor), *Advances in Nephrology*, 8, 297–319 (1979).

*Primary Examiner*—Richard A. Schwartz
*Attorney, Agent, or Firm*—Wegner & Bretschneider

[57] ABSTRACT

Novel imidazole-5-acetic acid derivatives of the formula:

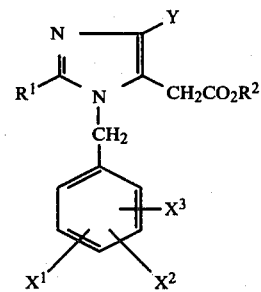

wherein $R^1$ is lower alkyl, cycloalkyl or, phenyl which may be substituted with one to three of halogen, nitro, amino, mono(lower alkyl)amino, di(lower alkyl)amino, lower alkyl, lower alkoxyl, benzyloxyl or/and hydroxyl; $X^1$, $X^2$ and $X^3$ are each hydrogen, halogen, nitro, amino, lower alkyl, lower alkoxyl, benzyloxyl or hydroxyl; Y is halogen and $R^2$ is hydrogen or lower alkyl; provided that $X^1$ is halogen, lower alkyl, lower alkoxyl, benzyloxyl or hydroxyl when $R^1$ is unsubstituted or substituted phenyl only with one halogen, di(-lower alkyl)amino, lower alkyl or lower alkoxyl, and its salts have hypotensive activity.

17 Claims, No Drawings

HYPOTENSIVE IMIDAZOLE-5-ACETIC ACID DERIVATIVES

The present invention relates to novel imidazole derivatives which are of value as medicines and to their production and use. More particularly, the present invention provides compounds of the formula (I):

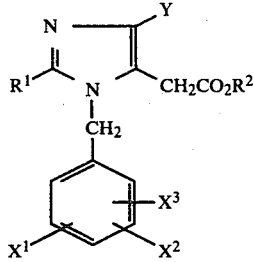

wherein $R^1$ is lower alkyl, cycloalkyl or, phenyl which may be substituted with one to three groups including halogen, nitro, amino, mono(lower alkyl)amino, di(lower alkyl)amino, lower alkyl, lower alkoxyl, benzyloxyl or/and hydroxyl; $X^1$, $X^2$ and $X^3$ are each hydrogen, halogen, nitro, amino, lower alkyl, lower alkoxyl, benzyloxyl or hydroxyl; Y is halogen and $R^2$ is hydrogen or lower alkyl, provided that $X^1$ is halogen, lower alkyl, lower alkoxyl, benzyloxyl or hydroxyl when $R^1$ is unsubstituted or phenyl substituted only with one halogen, di(lower alkyl)amino, lower alkyl or lower alkoxyl, and its salts which have the antagonistic effect on angiotensin II and the hypotensive activity, and are useful as a hypotensive agent.

Referring to the formula (I), lower alkyl as $R^1$ may be either straight-chain or branched, being exemplified by methyl, ethyl, propyl, isopropyl, butyl, isobutyl, t-butyl, pentyl, isopentyl, hexyl and heptyl, and those having 1 to 6 carbon atoms are particularly preferred; cycloalkyl as $R^1$ includes cyclopropyl, cyclobutyl, cyclopentyl, cyclohexyl, etc., and in particular, those having 4 to 6 carbon atoms are preferable; and phenyl as $R^1$ may have, as substituents in its optional positions, one to three, either the same or different, of halogen, nitro, amino, mono(lower alkyl)amino, di(lower alkyl)amino, lower alkyl, lower alkoxyl, benzyloxyl or/and hydroxyl. The halogen as such substituent is preferably chlorine and bromine, while the lower alkyl in the mono(lower alkyl)amino, di(lower alkyl)amino, lower alkyl and lower alkoxyl are preferably the same as the examples mentioned for the lower alkyl as $R^1$.

Halogen as $X^1$, $X^2$ and $X^3$ is preferably chlorine and bromine, while lower alkyl and lower alkyl in lower alkoxyl may be either straight-chain or branched and are in particular preferably those having 1 to 4 carbon atoms. Halogen as Y is preferably chlorine and bromine and among them chlorine is most preferable.

Among the compounds (I), preferable are the compounds where $R^1$ is the lower alkyl having 1 to 6 carbon atoms, phenyl having only one nitro, amino or hydroxyl, or phenyl having two to three of halogen, lower alkyl, lower alkoxyl, mono(lower alkyl)amino, di(lower alkyl)amino, amino, nitro, benzyloxyl or/and hydroxyl.

In the scope of the invention are compounds, wherein $R^1$ is unsubstituted phenyl, and $X^1$ is $C_{1-4}$ alkyl, $X_2$ is $C_{1-4}$ alkoxyl and $X_3$ is hydrogen. Also in the scope of the invention are compounds, wherein $R^1$ is phenyl substituted with two to three of halogen, mono(lower alkyl)amino, di(lower alkyl)amino, lower alkyl, lower alkoxyl, benzyloxyl or/and hydroxyl, and $X^1$, $X^2$ and $X^3$ are each hydrogen.

The compound (I) can be advantageously produced, for example, by solvolyzing a compound of the formula (II):

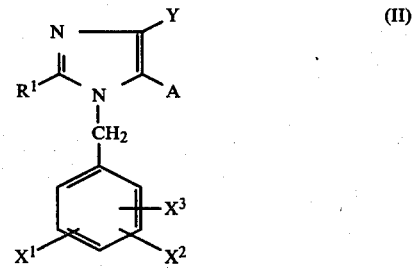

wherein $R^1$, $X^1$, $X^2$ and $X^3$ are as defined above and A is cyanomethyl or $\beta,\beta$-disubstituted vinyl designated with one of the following formulas (III a), (III b) and (III c):

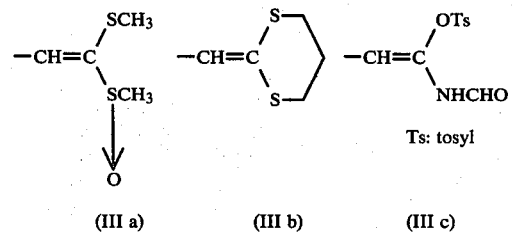

Ts: tosyl

As the solvolysis, either of hydrolysis and alcoholysis may be employed. Hydrolysis produces the compound (I) where $R^2$ is hydrogen, whereas alcoholysis affords the compound where $R^2$ is lower alkyl.

The hydrolysis of compound (II) wherein A is cyanomethyl is normally carried out in the presence of an acid or alkali. Among preferred examples of the acid are mineral acids such as sulfuric acid and hydrochloric acid. The concentration of such mineral acid in the reaction system is preferably about 40 to 60% for sulfuric acid and about 10 to 30% for hydrochloric acid, and in cases in which the compound (I) is less soluble in these acids, about 30 to 50% of acetic acid is advantageously allowed to coexist. Desired examples of the alkali include alkali metal hydroxides such as sodium hydroxide and potassium hydroxide, and the solvent which is advantageously used is for example aqueous methanol, aqueous ethanol, etc. The hydrolysis reaction proceeds under heating, and is normally conducted desirably at a temperature of about 50° to 160° C. for 2 to 12 hours. The compound (I) where $R^2$ is hydrogen, as obtained in this manner, can be derived through esterification into the compound (I) having lower alkyl as $R^2$. The esterification is conducted for example by heating the compound (I) where $R^2$ is hydrogen in a solvent containing the alcohol corresponding to the desired alkyl in the presence of an acid catalyst (e.g. sulfuric acid, hydrogen chloride, methanesulfonic acid, etc.).

The alcoholysis of compound (II) wherein A is cyanomethyl is normally carried out by heating it in an absolute or aqueous alcohol corresponding to lower alkyl as $R^2$ with addition of an acid, or further hydrolyzing, if necessary, and imino ether produced as an intermediate. As preferable examples of such acid may be mentioned inorganic acids such as hydrogen chloride and hydrogen bromide and organic acids such as p-toluenesulfonic acid, and these are desirably used in the proportion of about 1 to 10 the molar ratio of the compound (II). The reaction is preferably conducted under heating at about 50° to 100° C. for 1 to 10 hours. The resulting compound (I) where $R^2$ is lower alkyl can also be derived through hydrolysis into the compound (I) where $R^2$ is hydrogen. The hydrolysis is accomplished preferably by heating, with use of an alkali such as sodium hydroxide and potassium hydroxide, in a solvent such as aqueous methanol and aqueous ethanol at 20° to 100° C. for 5 to 20 hours. As the solvolysis procedure for compound (II) wherein A is $\beta,\beta$-disubstituted vinyl, either hydrolysis or alcoholysis may be employed. In the hydrolysis, hydrochloric acid, sulfuric acid of about 10 to 40% or p-toluene sulfonic acid of about 0.5 to 10 the molar ratio of the compound (III) is used and, in cases in which (II) is less soluble in these solvents, acetic acid or 1,2-dimethoxyethane is advantageously allowed to coexist in the range of about 30 to 50%. The alcoholysis is normally carried out easily by passing hydrogen chloride through the compound (II), at a temperature of about 0° to 30° C., in an alcohol corresponding to the lower alkyl group as $R^2$.

In the solvolysis of the compounds (II), the substituents on the substituted phenyl as $R^1$, in some instances, undergo changes. For example, hydrolysis in hydrochloric acid of the compound (IIa) where $R^1$ is a 4-dimethylamino-3,5-dinitrophenyl yields the compound (Ia) where nitrile is converted into the carboxyl, with the dimethylamino changed to chlorine.

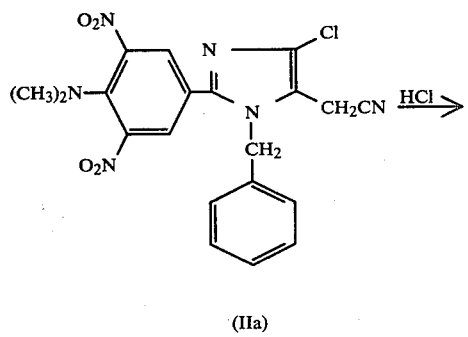

(IIa)

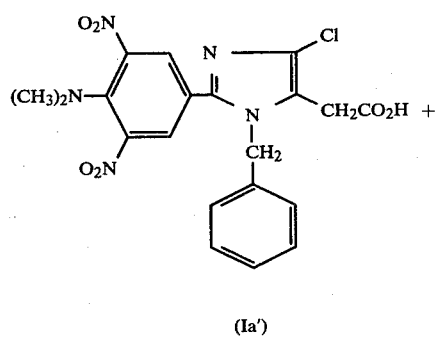

(Ia')

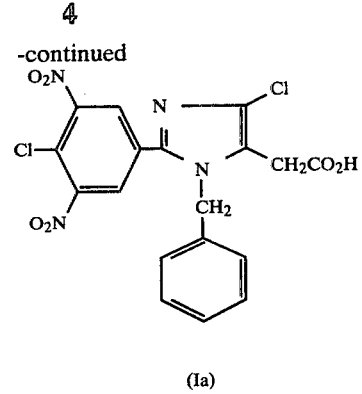

(Ia)

Starting from the compound (IIb) where $R^1$ is a 4-acylaminophenyl, further, there is obtained the compound (Ib) having a 4-aminophenyl through hydrolysis with hydrochloric acid as mentioned above.

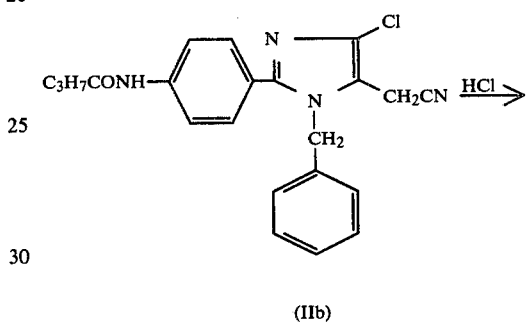

(IIb)

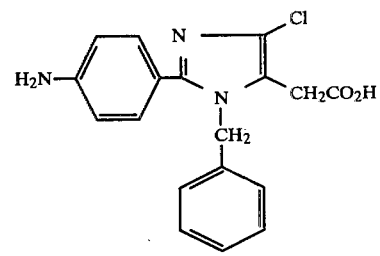

(Ib)

From the resulting compound (I) where nitro and/or a benzyloxyl group are present on the phenyl as $R^1$ and/or as $X^1$, $X^2$ and $X^3$, there can be derived the compound (I) having an amino and/or hydroxyl through reduction of these groups. As examples of the reduction procedure there may be mentioned the procedures normally employed such as the tin-hydrochloric acid, iron-hydrochloric acid, zinc-acetic acid and catalytic reductions, and the catalysts for the catalytic reduction are preferably 5 to 10% palladium-carbon, Raney nickel, platinum, etc.

From the resulting compound (I) where there is benzyloxyl or lower alkoxyl on the phenyl as $R^1$ and/or as $X^1$, $X^2$ and $X^3$, there can be derived the compound (I) having a hydroxyl through hydrolysis of such groups. The preferred example of the hydrolysis includes the procedure of heating under reflux in ethanol saturated with hydrochloric acid or 30 to 50% hydrobromic acid for 2 to 6 hours.

The compound (I) produced in this manner can be easily isolated from the reaction mixture by the conventional separation and purification procedures such as dilution with water, extraction, concentration, neutralization and recrystallization. These compounds (I) can be obtained, by the procedures conventional per se, as physiologically acceptable salts with acids or bases. As examples of such salts there may be mentioned acid addition salts formed with inorganic acids (e.g. hydrochloric acid, hydrobromic acid, sulfuric acid, etc.) and with organic acids (e.g. acetic acid, propionic acid, maleic acid, succinic acid, malic acid, etc.), salts with bases such as ammonium salt and salts formed with alkali metals or alkaline earth metals (e.g. sodium, potassium, calcium, etc.).

The compounds (I) produced in this manner as well as their salts, being low in toxicity and suppressing the vaso-constrictive and blood-pressure elevating actions of angiotensin II, exhibit excellent hypotensive activity toward animals, particularly mammals (e.g. dogs, rabbits, rats, men, etc.), and are of value as a treatment agent for hypertension. When one of the compounds is employed as such a hypotensive agent, the compound (I) or its salts as mentioned above can be orally or parenterally administered, either as such or in the form of powder, granule, tablet, capsule, injection, etc., prepared by mixing with a suitable, pharmaceutically acceptable carrier, vehicle or diluent. Though the quantity of the compound to be administered varies depending upon the kinds of diseases to be treated, symptoms, subjects and routes of administration, etc., it is preferably given in a daily dose of 10 to 100 mg for oral administration and 5 to 50 mg for intravenous injection, 2 to 3 times a day, in case of administration to adult humans as a treatment agent for essential hypertension.

The starting compounds (II) wherein A is cyanomethyl to be used in the present invention can be produced for example in accordance with the procedure of Japanese Patent Application No. 057912/78 (U.S. patent application Ser. No. 36,645 fruited to U.S. Pat. No. 4,207,324) through the route given below.

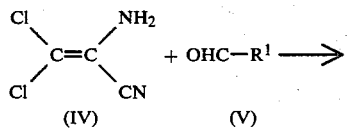

(IV) (V)

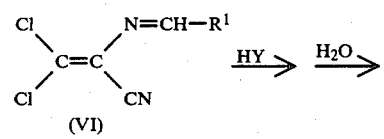

(VI)

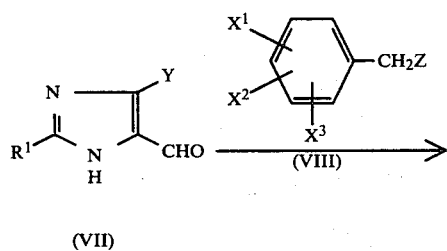

(VII)

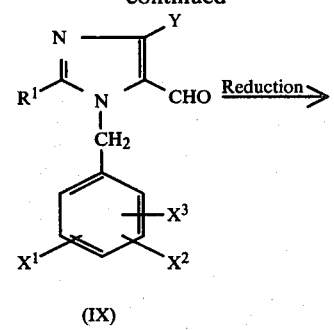

(IX)

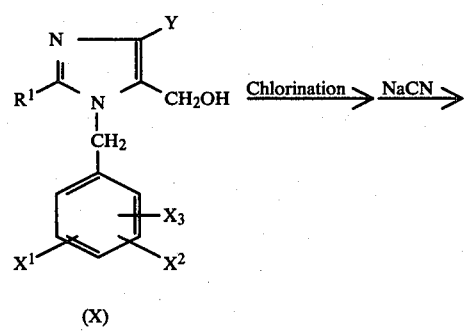

(X)

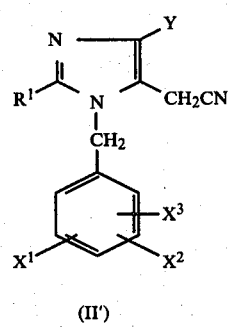

(II')

wherein $R^1$, $X^1$, $X^2$, $X^3$ and Y are as defined above; Z is halogen.

On the other hand, the starting compounds (II) wherein A is $\beta,\beta$-disubstituted vinyl can be produced from the corresponding aldehyde (IX) and following respective reagent in accordance with the method thereon;

| | |
|---|---|
| Compound (II): wherein A is (III a) | formaldehyde dimethylthioacetal S-oxide by the FAMSO method [Tetrahedron Letters, 1383(1972)] |
| Compound (II): wherein A is (III b) | 1,3-dithian by the dithian method [J. Med. Chem., 15, 1297(1972)] |
| Compound (II): wherein A is (III c) | p-toluenesulfonylmethylisocyanide by the TOSMIC method [Ang. Chem. Int. Ed., 11, 311 (1972)] |

In addition, the intermediate (X) can be also produced by the route given below.

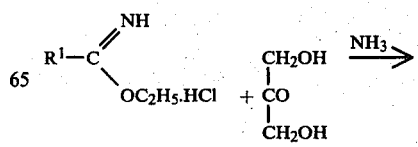

-continued

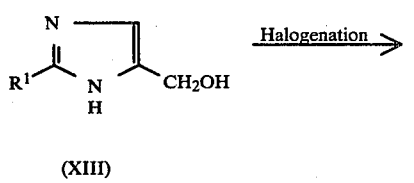

(XIII)

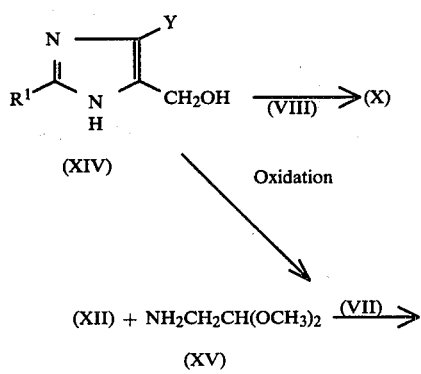

(XIV)

Oxidation (XII) + NH₂CH₂CH(OCH₃)₂ —(VII)→
(XV)

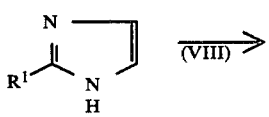

(XVI)

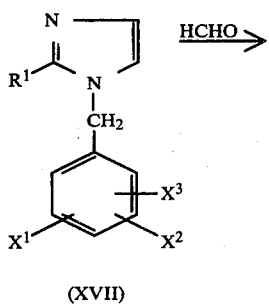

(XVII)

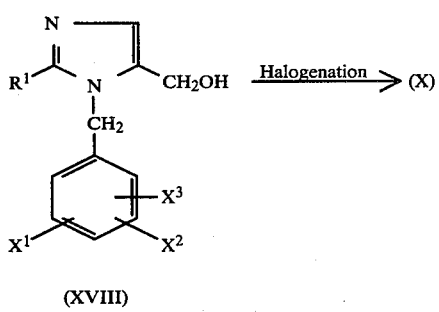

(XVIII)

wherein each of the symbols in the formulas is as defined above.

The compound (XIII) is produced for example by the procedure described in "Archiv der Pharmazie", 307, 470 (1974). The halogenation of the compound (XIII) is preferably accomplished by reacting with 1 to 2 equivalents of N-halogenosuccinimide in a solvent such as dioxane and methylcellosolve at a temperature of about 40° to 100° C. for 1 to 10 hours. Reaction of the compound (XIV) obtained in this manner with benzyl halogenide is conducted in a solvent in the presence of acid acceptor. Examples of the acid acceptors which are useful include potassium carbonate, sodium carbonate, sodium hydride, sodium methylate and sodium ethylate, and in the case of the last three, it is recommended to treat in advance with (XIV) to form the sodium salts. As preferred examples of the solvent may be mentioned dimethylformamide and dimethylsulfoxide. The reaction is preferably conducted under stirring at a temperature of about 20° to 100° C. for 1 to 10 hours. In the reaction, there is normally produced an isomer designated by (X'), in addition to the compound (X).

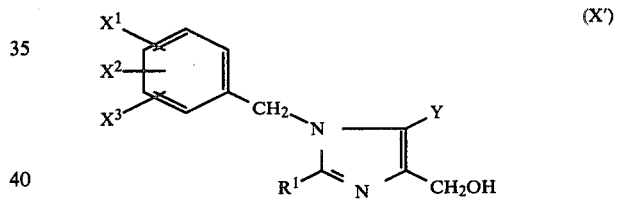

(X')

Separation of (X) from (X') is carried out by the conventional chemical procedures such as recrystallization and chromatography. Oxidation of the compound (XIV) to the compound (VII) is conducted in tetrahydrofuran with use of anhydrous chromic acid-silica gel.

The compound (XVI) can be produced for example by the procedure described in "The Journal of Chemical Society", 4225 (1957), while the compound (XVIII) can be produced for example in accordance with the procedure described in "Recueil", 91, 1385 (1972). The compound (XVIII) obtained in this manner can be derived into (X) by the procedure similar to the halogenation reaction of (XIII).

In various synthesis routes as mentioned above, $R^1$, $X^1$, $X^2$ and $X^3$ do not necessarily remain the same from the starting compound to the final objective compound, but they can be, as a matter of course, changed to appropriate ones through the known reactions in the intermediate steps. These are specifically exemplified below.

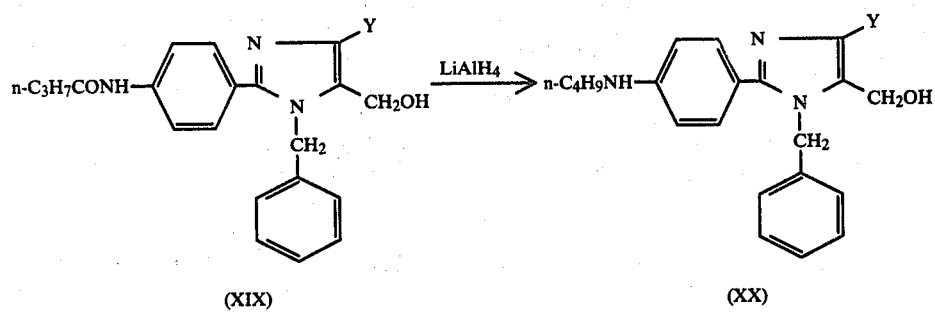
(XIX) → (XX)
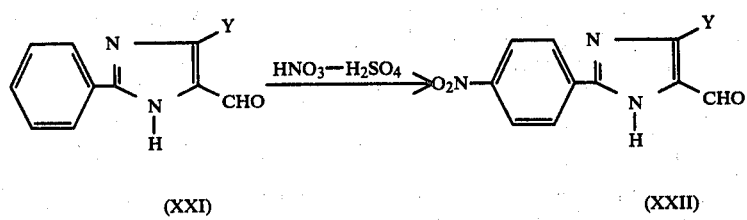
(XXI) → (XXII)
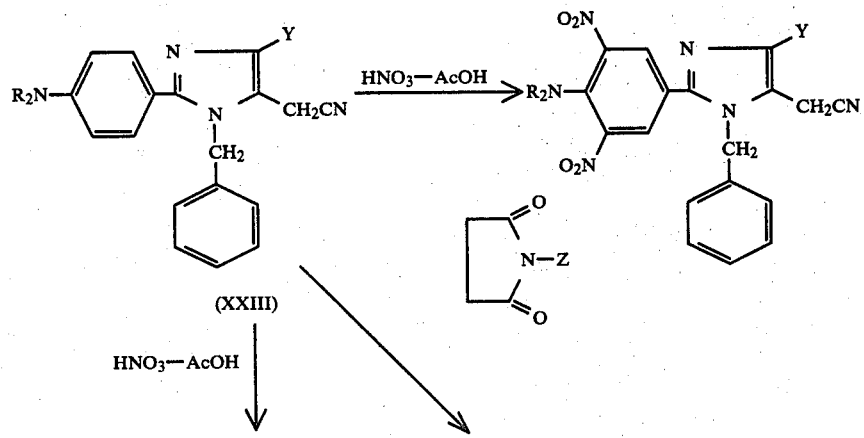
(XXIII) → (XXIV)
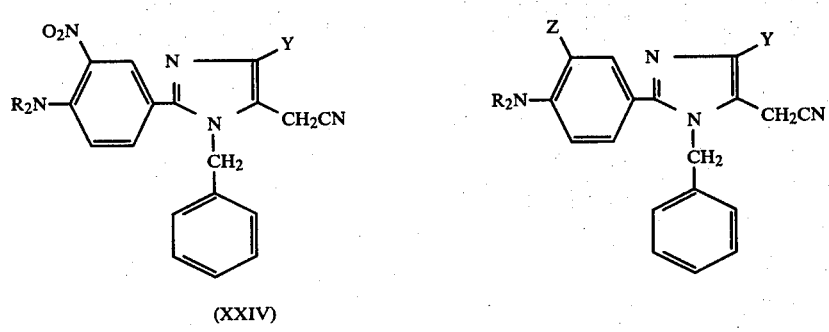
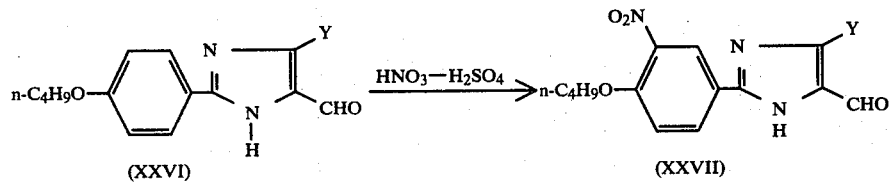
(XXVI) → (XXVII)

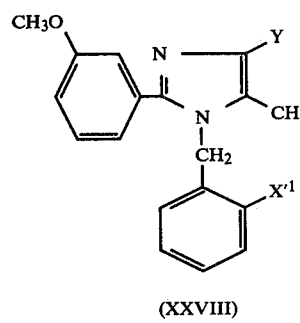

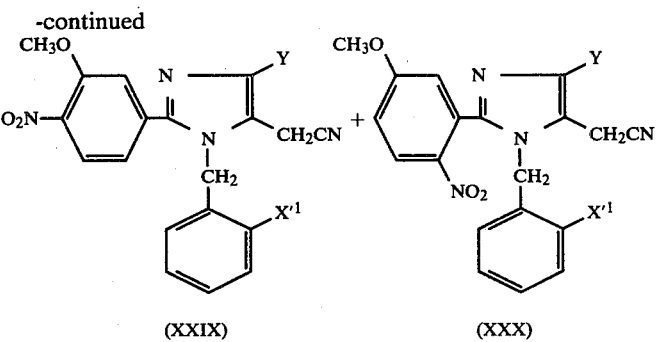

(XXVIII)                    (XXIX)                    (XXX)

wherein Y is as defined above; R is lower alkyl; $X^{1'}$ is halogen or nitro.

The present invention is more specifically illustrated by the following Examples, Experiment Examples and Reference Examples; however, it goes without saying that these are not intended to limit the present invention.

EXAMPLE 1

7 g of 1-benzyl-4-chloro-5-cyanomethyl-2-(4-nitrophenyl)imidazole was boiled in 60 ml of 6 N-hydrochloric acid for 4 hours. The reaction solution was diluted with 150 ml of water, and the deposited precipitate was dissolved by heating in 50 ml of 90% ethanol. Water was added little by little until cloudiness was developed, followed by allowing the solution to cool. There was obtained 5.6 g of 1-benzyl-4-chloro-2-(4-nitrophenyl)imidazole-5-acetic acid deposited as yellow, prism-formed crystals, m.p. 180°–183° C.

| Elementary analysis, for $C_{18}H_{14}N_3O_4Cl$ | | | | |
|---|---|---|---|---|
| | C (%) | H (%) | N (%) | Cl (%) |
| Calcd. | 58.15 | 3.79 | 11.30 | 9.54 |
| Found | 58.29 | 3.77 | 11.11 | 9.77 |

EXAMPLE 2

1.9 g of 1-(2-chloro-5-nitrobenzyl)-4-chloro-5-cyanomethyl-2-phenylimidazole was boiled in a mixed solution of 12 ml of concentrated hydrochloric acid and 12 ml of glacial acetic acid for 3 hours. The reaction solution was concentrated to dryness under reduced pressure, and 50 ml of water was added to the residue, resulting in the formation of a colorless powder. The residue was dissolved in 30 ml of heated ethanol, and 30 ml of water was added. Upon cooling, there was obtained 1.7 g of 1-(2-chloro-5-nitrobenzyl)-4-chloro-2-phenylimidazole-5-acetic acid as colorless, prism-formed crystals. m.p. 200°–205° C.

| Elementary analysis, for $C_{18}H_{13}N_3O_4Cl_2$ | | | | |
|---|---|---|---|---|
| | C (%) | H (%) | N (%) | Cl (%) |
| Calcd. | 53.22 | 3.23 | 10.34 | 17.44 |
| Found | 53.32 | 3.03 | 10.44 | 17.44 |

EXAMPLE 3

3.8 g of 1-(2,4-dichlorobenzyl)-4-chloro-2-phenyl-5-cyanomethylimidazole was boiled in 40 ml of 6 N-hydrochloric acid for 11 hours. After cooling, the crystals deposited from the solution were recrystallized from acetonitrile, thus yielding 3.5 g of 1-(2,4-dichlorobenzyl)-4-chloro-2-phenylimidazole-5-acetic acid hydrochloride as colorless, needle-formed crystals, m.p. 209°–211° C.

| Elementary analysis, for $C_{18}H_{13}N_2O_2Cl_3 \cdot HCl \cdot H_2O$ | | | | |
|---|---|---|---|---|
| | C (%) | H (%) | N (%) | Cl (%) |
| Calcd. | 48.02 | 3.58 | 6.22 | 31.50 |
| Found | 48.14 | 3.50 | 6.29 | 31.26 |

EXAMPLES 4–35

By the procedures as described in Examples 1, 2 and 3, there were obtained the compounds given below.

TABLE 1

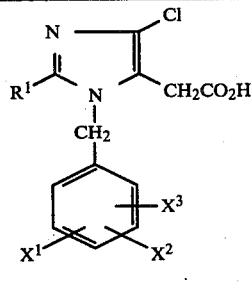

| Example No. | $R^1$ | $X^1$ | $X^2$ | $X^3$ | m.p. (°C.) |
|---|---|---|---|---|---|
| 4 | phenyl | 4-$CH_3$ | H | H | 100–105 |
| 5 | phenyl | 2-$CH_3$ | H | H | 211–212 |
| 6 | phenyl | 4-Cl | H | H | 203–205 (decomp.) |
| 7 | phenyl | 2-Cl | H | H | 198–200 (decomp.) |
| 8 | phenyl | 2-Cl | H | 6-Cl | 185–186 |
| 9 | phenyl | 2-Cl | H | 6-F | 210–214 |
| 10 | phenyl | 2-Cl | 5-$NH_2$ | H | 210–215 (decomp.) |

TABLE 1-continued

Structure: R¹–C(=N)–N(–CH₂–C₆H₃(X¹)(X²)(X³))–C(=C(Cl))–CH₂CO₂H (imidazole with 4-Cl and 5-CH₂CO₂H, 1-benzyl substituted with X¹, X², X³)

| Example No. | R¹ | X¹ | X² | X³ | m.p. (°C) |
|---|---|---|---|---|---|
| 11 | phenyl | 2-Br | H | H | 229–230 (decomp.) |
| 12 | 4-(C₄H₉NH)-phenyl | H | H | H | 131–135 |
| 13 | 2-NO₂-phenyl | H | H | H | 207–210 (hydrochloride) |
| 14 | 3,4-methylenedioxyphenyl | H | H | H | 175–177 |
| 15 | 4-(CH₃)₂N-3-O₂N-phenyl | H | H | H | 187–190 |
| 16 | 3,5-bis(O₂N)-4-(CH₃)₂N-phenyl | H | H | H | 190–192 |
| 17 | 2-Cl-4-(C₂H₅)₂N-phenyl | H | H | H | 165–170 |
| 18 | 2-Br-4-(CH₃)₂N-phenyl | H | H | H | 202–204 |
| 19 | 2-Cl-4-(CH₃)₂N-phenyl | H | H | H | 205–207 |
| 20 | 3-CH₃O-phenyl | 2-Cl | H | H | 147–148 |
| 21 | 2-Cl-4-CH₃O-6-Cl-phenyl | 2-NO₂ | H | H | (decomp.) (potassium salt) |
| 22 | 2-O₂N-4-CH₃O-phenyl | 2-NO₂ | H | H | 102–105 |
| 23 | CH₃ | H | H | H | 189–191 |
| 24 | C₂H₅– | H | H | H | 197–199 |
| 25 | i-C₃H₇– | H | H | H | 181–182 |
| 26 | n-C₄H₉– | H | H | H | 151–152 |
| 27 | n-C₄H₉– | 2-Cl | H | H | 172–173 |
| 28 | n-C₄H₉– | 2-NO₂ | H | H | 188–190 |
| 29 | n-C₃H₇– | H | H | H | 189–191 |
| 30 | t-C₄H₉– | H | H | H | 202–204 |
| 31 | n-C₅H₁₁– | H | H | H | 110–112 |
| 32 | n-C₅H₁₁ | 2-Cl | H | H | 137–139 |
| 33 | n-C₆H₁₃– | 2-Cl | H | H | 157–159 |
| 34 | cyclopentyl | H | H | H | 164–165 |
| 35 | cyclohexyl | H | H | H | 117–119 |

EXAMPLE 36

1.7 g of 4-chloro-1-(3-methoxybenzyl)-2-phenyl-5-cyanomethylimidazole was boiled in a mixed solution of 20 ml of ethanol and 10 ml of 1 N-sodium hydroxide for 10 hours. The reaction solution was evaporated to dryness under reduced pressure, and the residue was dissolved in 50 ml of water. After washing with 50 ml of chloroform, 10 ml of 1 N-hydrochloric acid was added to the water layer, resulting in the precipitate deposited. The precipitate was dissolved in 20 ml of 90% ethanol, and water was added little by little, thus yielding 1.3 g of 4-chloro-1-(3-methoxybenzyl)-2-phenylimidazole-5-acetic acid as colorless, needle-formed crystals, m.p. 135°–138° C.

| | Elementary analysis, for C₁₉H₁₇N₂O₃Cl | | | |
|---|---|---|---|---|
| | C (%) | H (%) | N (%) | Cl (%) |
| Calcd. | 63.95 | 4.80 | 7.85 | 9.93 |
| Found | 64.22 | 4.72 | 7.89 | 9.91 |

EXAMPLE 37–49

There were obtained the following compounds in accordance with the procedure of Example 36.

TABLE 2

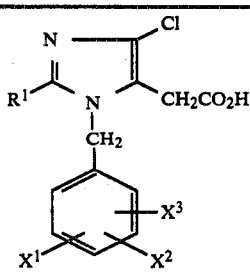

| Example No. | R¹ | X¹ | X² | X³ | m.p. (°C.) |
|---|---|---|---|---|---|
| 37 | C₆H₅- | 2-CH₃O | H | H | 189–190 |
| 38 | C₆H₅- | 4-CH₃O | H | H | 205–210 (decomp.) |
| 39 | C₆H₅- | 4-C₂H₅O | H | H | 210–212 |
| 40 | C₆H₅- | 4-n-C₄H₉O | H | H | 153–156 |
| 41 | C₆H₅- | 4-C₆H₅CH₂O | H | H | 209–211 |
| 42 | C₆H₅- | 3-CH₃O | H | 4-CH₃O | 207–208 (decomp.) |
| 43 | C₆H₅- | 3-CH₃ | H | 4-CH₃O | 199–200 (decomp.) |
| 44 | 2,3-(CH₃O)₂C₆H₃- | H | H | H | 230–232 |
| 45 | 3-CH₃O-2-CH₃-C₆H₃- | H | H | H | 199–200 |
| 46 | 3-CH₃O-2-C₆H₅CH₂O-C₆H₃- | H | H | H | 203–205 |
| 47 | C₆H₅- | 3-CH₃O | 4-CH₃O | 5-CH₃O | 161–162 |
| 48 | n-C₄H₉- | H | 4-n-C₄H₉O | H | 102–103 |
| 49 | 2,3,4-(CH₃O)₃C₆H₂- | H | H | H | 159–161 |

EXAMPLE 50

In 100 ml of methanol was dissolved 1.8 g of 4-chloro-1-(4-methylbenzyl)-2-phenylimidazole-5-acetic acid, and 0.5 ml of concentrated sulfuric acid was added to the solution to boil for 2 hours. The reaction solution was evaporated to dryness under reduced pressure, and 50 ml each of ethyl acetate and a 10% aqueous sodium bicarbonate solution were added to the residue to shake. The ethyl acetate layer, after washing with water, was evaporated to dryness under reduced pressure. The residue was dissolved in a small amount of methanol and there was obtained, upon standing, 1.5 g of methyl 4-chloro-1-(4-methylbenzyl)-2-phenylimidazole-5-acetate as colorless, prism-formed crystals, m.p. 92°–95° C.

| Elementary analysis, for $C_{20}H_{19}N_2O_2Cl$ | | | |
|---|---|---|---|
| | C (%) | H (%) | N (%) | Cl (%) |
| Calcd. | 67.70 | 5.39 | 7.89 | 9.99 |
| Found | 67.34 | 5.56 | 7.71 | 9.61 |

EXAMPLE 51

1 g of 1-benzyl-2-n-butyl-4-chloro-5-cyanomethylimidazole was heated in 20 ml of ethanol containing 1 g of hydrogen chloride in a sealed tube at 100° C. for 2 hours. 0.5 ml of water was added to the reaction solution, which was then boiled for 1 hour and evaporated to dryness under reduced pressure. The residue was dissolved in 50 ml of ethyl acetate and, after washing with aqueous sodium bicarbonate, the ethyl acetate layer was evaporated to dryness, and chromatographed on a column of 30 g of silica gel. The column was eluted with benzene-ethyl acetate (4:1), and the main fractions were evaporated to dryness. The residue was dissolved in 1 ml ethanol saturated with hydrogen chloride, and crystallized by adding petroleum ether. After further adding ethyl acetate to separate out in the fully crystallized condition, there was obtained 300 mg of ethyl 1-benzyl-2-n-butyl-4-chloroimidazole-5-acetate hydrochloride. m.p. 101°–103° C.

| Elementary analysis, for $C_{18}H_{23}N_2O_2Cl \cdot HCl \cdot \frac{1}{2}H_2O$ | | | |
|---|---|---|---|
| | C (%) | H (%) | N (%) |
| Calcd. | 56.85 | 6.62 | 7.36 |
| Found | 57.02 | 6.42 | 7.40 |

EXAMPLE 52

In 5 ml of tetrahydrofuran was dissolved 1.5 g of 4-chloro-1-(2-fluorobenzyl)-2-phenyl-5-formylimidazole, and the solution was stirred and refluxed. 1 ml each of formaldehyde dimethylthioacetal S-oxide and 35% methanol solution of benzyltrimethyl ammonium hydroxide were dissolved in 3 ml of tetrahydrofuran to add dropwise to the above-mentioned solution over a 2-hour period. After adding was completed, the reaction solution was boiled for further 5 hours and evaporated to dryness under reduced pressure. 50 ml each of chloroform and water were added to the residue, and shaken to mix, followed by evaporating the chloroform layer to dryness to obtain a resinous material of 1-methylsulfinyl-1-methylthio-2-[4-chloro-1-(2-fluorobenzyl)-2-phenylimidazol-5-yl]ethylene. 5 ml of concentrated hydrochloric acid and 5 ml of glacial acetic acid were added to the material, and heated at 100° C. for 5 hours. The reaction solution was evaporated to dryness under reduced pressure, and 50 ml each of chloroform and a 10% aqueous sodium carbonate solution were added to the residue to shake to mix. The water layer was acidified by adding concentrated hydrochloric acid and extracted with 50 ml of chloroform. After evaporating the chloroform layer to dryness under reduced pressure, recrystallization of the residue from aqueous ethanol yielded 410 mg of 4-chloro-1-(2-fluorobenzyl)-2-phenylimidazole-5-acetic acid as colorless, prism-formed crystals, m.p. 144°–146° C.

| Elementary analysis, for $C_{18}H_{14}N_2O_2ClF$ | | | |
|---|---|---|---|
| | C (%) | H (%) | N (%) |
| Calcd. | 62.71 | 4.09 | 8.12 |
| Found | 62.74 | 4.33 | 7.87 |

EXAMPLE 53

In 30 ml of tetrahydrofuran was dissolved 4.5 g of 4-chloro-1-(2-methylbenzyl)-2-phenyl-5-formylimidazole, and the solution was stirred and refluxed. 6 ml of formaldehyde dimethylthioacetal S-oxide and 6 ml of a 35% methanol solution of benzyltrimethyl ammonium hydroxide were dissolved in 30 ml of tetrahydrofuran to add dropwise to the above-mentioned solution over a period of 12 hours. After adding was completed, the solution was boiled for further 18 hours, and evaporated to dryness under reduced pressure. 200 ml each of chloroform and water were added to the residue to shake for mixing, followed by evaporating the chloroform layer to dryness to obtain a resinous material of 1-methylsulfinyl-1-methylthio-2-[4-chloro-1-(2-methylbenzyl)-2-phenylimidazol-5-yl]ethylene. The material was dissolved in 100 ml of ethanol saturated with hydrogen chloride and allowed to stand at room temperature for 40 hours. The reaction solution was evaporated to dryness under reduced pressure, and the residue was chromatographed on a column of 80 g of silica gel, followed by eluting with chloroform. The main fractions were collected to evaporate to dryness under reduced pressure. Recrystallization of the residue from methanol yielded 1.5 g of methyl 4-chloro-1-(2-methylbenzyl)-2-phenylimidazole-5-acetate, m.p., 102°–105° C.

| Elementary analysis, for $C_{20}H_{19}N_2O_2Cl$ | | | |
|---|---|---|---|
| | C (%) | H (%) | N (%) | Cl (%) |
| Calcd. | 67.70 | 5.39 | 7.89 | 9.99 |
| Found | 67.29 | 5.71 | 7.52 | 9.58 |

EXAMPLE 54

1.4 g of 1-benzyl-4-chloro-2-(4-dimethylamino-3,5-dinitrophenyl)-5-cyanomethylimidazole was stirred in 30 ml of concentrated hydrochloric acid at 70° C. for 40 hours. The deposited yellow crystals were recovered by filtration, washed twice with concentrated hydrochloric acid and adequately with water, and recrystallized twice from 70% ethanol, thus yielding 0.9 g of 1-benzyl-4-chloro-2-(4-chloro-3,5-dinitrophenyl)imidazole-5-acetic acid as yellow-orange, needle-formed crystals, m.p. 100°–105° C.

| Elementary analysis, for $C_{18}H_{12}N_4O_6Cl_2 \cdot C_2H_5OH$ | | | |
|---|---|---|---|
| | C (%) | H (%) | N (%) | Cl (%) |
| Calcd. | 48.25 | 3.65 | 11.26 | 14.24 |
| Found | 48.28 | 3.56 | 11.36 | 14.15 |

EXAMPLE 55

1.7 g of 1-benzyl-4-chloro-2-(4-n-butyrylaminophenyl)-5-cyanomethylimidazole was stirred in a mixed solution of 9 ml each of concentrated hydrochloric acid, water and glacial acetic acid at 120° C. for 5 hours. The reaction solution was evaporated to dryness under reduced pressure, and the residue was dissolved in 20 ml of water, followed by adjusting to pH 4 with sodium bicarbonate. The deposited precipitate was recrytalized from 80% ethanol, thus resulting in 1.3 g of 1-benzyl-4-chloro-2-(4-aminophenyl)imidazole-5-acetic acid as colorless, needle-formed crystals, m.p. 120°–122° C.

| Elementary analysis, for $C_{18}H_{16}N_3O_2Cl \cdot H_2O$ | | | | |
|---|---|---|---|---|
| | C (%) | H (%) | N (%) | Cl (%) |
| Calcd. | 60.09 | 5.04 | 11.66 | 9.85 |
| Found | 60.00 | 5.05 | 11.76 | 9.66 |

EXAMPLE 56

In 100 ml of 80% ethanol was dissolved 1.8 g of 1-benzyl-4-chloro-2-(2-nitrophenyl)imidazole-5-acetic acid, and hydrogenated in the presence of 0.3 g to 10% palladium - carbon. The catalyst was filtered out and the filtrate, after adding 5 ml of 1 N-hydrochloric acid, was evaporated to dryness under reduced pressure, resulting in 1.3 g of 1-benzyl-4-chloro-2-(2-aminophenyl)imidazole-5-acetic acid hydrochloride as colorless powder, m.p. 115°–120° C.

| Elementary analysis, for $C_{18}H_{16}N_3O_2Cl \cdot HCl$ | | | | |
|---|---|---|---|---|
| | C (%) | H (%) | N (%) | Cl (%) |
| Calcd. | 57.15 | 4.53 | 11.11 | 18.74 |
| Found | 56.85 | 4.66 | 10.97 | 18.66 |

EXAMPLE 57

2.8 g of 1-benzyl-4-chloro-2-(4-benzyloxy-3-methoxyphenyl)-5-cyanomethylimidazole was boiled in a mixed solution of 45 ml of 6 N-hydrochloric acid and 10 ml of glacial acetic acid for 3.5 hours. The reaction solution was evaporated to dryness under reduced pressure, and the residue was dissolved in 30 ml of water. When the solution was made to pH 3 with sodium bicarbonate, there deposited 2 g of 1-benzyl-4-chloro-2-(4-hydroxy-3-methoxyphenyl)imidazole-5-acetic acid as colorless, prism-formed crystals, which were recovered by filtration. m.p. 179°–181° C.

| Elementary analysis, for $C_{19}H_{17}N_2O_4Cl$ | | | |
|---|---|---|---|
| | C (%) | H (%) | N (%) |
| Calcd. | 61.21 | 4.60 | 7.51 |
| Found | 61.06 | 4.51 | 7.56 |

EXAMPLE 58

1 g of 1-benzyl-4-chloro-2-(4-n-butoxyphenyl)imidazole-5-acetic acid was boiled in 14 ml of 48% hydrobromic acid for 2 hours, and addition of 15 ml of water, followed by allowing the solution to stand, resulted in crystals deposited. Recrystallization of the crystals from aqueous ethanol yielded 0.5 g of 1-benzyl-4-chloro-2-(4-hydroxyphenyl)imidazole-5-acetic acid as colorless, prism-formed crystals, m.p. 140°–145° C.

| Elementary analysis, for $C_{18}H_{15}N_2O_3Cl$ | | | | |
|---|---|---|---|---|
| | C (%) | H (%) | N (%) | Cl (%) |
| Calcd. | 63.10 | 4.38 | 8.17 | 10.34 |
| Found | 62.76 | 4.61 | 8.01 | 9.77 |

EXAMPLE 59

1 g of 1-benzyl-4-chloro-2-(3-methoxyphenyl)imidazole-5-acetic acid was boiled in 14 ml of 48% hydrobromic acid for 2 hours. The reaction solution was evaporated to dryness and, when water was added to the residue, there separated out white powder. The powder was dissolved in 10 ml of hot ethanol, and water was added to the solution until turbidity was developed. After allowing it to stand, there was obtained 0.8 g of 1-benzyl-4-chloro-2-(3-hydroxyphenyl)imidazole-5-acetic acid as colorless, prism-formed crystals, m.p. 220°–222° C.

| Elementary analysis, for $C_{18}H_{15}N_2O_3Cl$ | | | | |
|---|---|---|---|---|
| | C (%) | H (%) | N (%) | Cl (%) |
| Calcd. | 63.10 | 4.38 | 8.17 | 10.34 |
| Found | 63.19 | 4.20 | 8.04 | 10.18 |

EXAMPLE 60–62

There were obtained the following compounds in accordance with the procedures of Examples 58 and 59.

TABLE 3

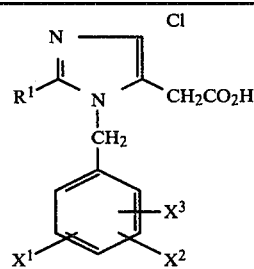

| Example No. | $R^1$ | $X^1$ | $X^2$ | $X^3$ | m.p. (°C.) |
|---|---|---|---|---|---|
| 60 | ![2-OH phenyl] | H | H | H | 175–178 |
| 61 | ![3,4-di-OH phenyl] | H | H | H | 153–155 |
| 62 | ![4-OH-3-CH3 phenyl] | H | H | H | 197–199 |

EXAMPLE 63

1.3 g of 1-(4-benzyloxybenzyl)-4-chloro-2-phenylimidazole-5-acetic acid was boiled in 50 ml of ethanol saturated with hydrogen chloride for 7 hours. The reaction solution was evaporated to dryness under reduced pressure, and 50 ml each of a 5% aqueous sodium carbonate solution and ethyl acetate were added to the residue to shake to mix. The ethyl acetate layer was washed and evaporated to dryness under reduced pressure. Recrystallization of the residue from 10 ml of acetonitrile yielded 140 mg of 1-(4-hydroxybenzyl)-4-chloro-2-phenylimidazole-5-acetic acid as colorless crystals, m.p. 196°–199° C.

| Elementary analysis, for C20H19N2O3Cl | | |
|---|---|---|
| | C (%) | N (%) | N (%) |
| Calcd. | 64.77 | 5.16 | 7.56 |
| Found | 64.95 | 5.28 | 7.31 |

EXAMPLE 64

In 5 ml of ethanol was dissolved 680 mg of 4-chloro-2-phenyl-1-(4-methylbenzyl)imidazole-5-acetic acid, and a solution of 80 mg of sodium hydroxide in 1 ml of water was added to the solution. The mixed solution was evaporated to dryness under reduced pressure, and the residue was dissolved in 5 ml of ethanol. Upon addition of 30 ml of ether to the solution, there was obtained 0.5 g of sodium salt of the above-mentioned compound as colorless crystalline powder, m.p. 287°–290° C.

EXAMPLE 65

To the solution of 6 g of 1,3-dithian in 66 ml of tetrahydrofuran was added dropwise n-butyllithium in 30 ml of hexane (1.6 M) under nitrogen atmosphere and cooling (−25° C.) during 15 minutes period. After the reaction mixture was stirred for 2 hours at −15° C., was added under ice-cooling 13.6 g of 1-benzyl-4-chloro-5-formyl-2-(4-nitrophenyl)imidazole in 215 ml of tetrahydrofuran during 1 hour period, and then was stirred for 20 hours under ice-cooling. The reaction mixture was evaporated to dryness under reduced pressure and 200 ml of chloroform was added to the resulting residue and was washed with 5% hydrochloric acid, water and saturated aqueous NaCl solution in this order. The solution was dried over sodium sulfate and evaporated to dryness under reduced pressure and the residue was dissolved 200 ml of benzene and was refluxed for 30 minutes after addition of 1.6 g p-toluenesulfonic acid using water separator to catch the resulting water. The reaction mixture was washed with 5% sodium bicarbonate, water and saturated aqueous NaCl solution in this order and evaporated to dryness under reduced pressure. The resulting residue (20 g) of 2-[1-benzyl-4-chloro-2-(4-nitrophenyl)imidazol-5-yl methylidene]-1,3-dithiane was refluxed for two hours in 210 ml of acetic anhydride and 70 ml of concentrated hydrochloric acid and concentrated to dryness under reduced pressure. The residue was dissolved in 200 ml of chloroform and washed with water and then extracted twice with 200 ml portion of 1 N-NaOH.

The combined extract was washed with chloroform and adjusted to pH 2 with hydrochloric acid and then extracted twice with 100 ml portion of chloroform. The chloroform layer was washed with water and concentrated to dryness under reduced pressure. The residue was recrystalized twice from 80% ethanol to give 1.2 g of 1-benzyl-4-chloro-2-(4-nitrophenyl)imidazole-5-acetic acid as yellow prism crystal. m.p. 180°–183° C.

EXAMPLE 66

In 35 ml of t-butanol was dissolved 975 mg of potassium and concentrated to dryness under reduced pressure. The resulting residue was dissolved in 25 ml of DMSO and 0.5 ml of t-butanol. The solution was added to DMSO solution of 2.92 g of p-toluenesulfonylmethylisocyanide and 1.7 g of 1-(4-chlorobenzyl)-4-chloro-5-formyl-2-phenylimidazole under ice-cooling and then stirred for 1 hour under ice-cooling and 18 hour at room temperature. The reaction mixture was poured into 150 ml of water and extracted 3 times with 100 ml portion of ether. Combined ether layer was washed with water and concentrated to dryness under reduced pressure, the resulting residue was chromatographed on 60 g of silica gel and eluted with chloroform. The main fraction was concentrated to dryness under reduced pressure and the residue (0.3 g) of 1-formylamino-1-p-toluenesulfonyl-2-[1-(4-chlorobenzyl)-4-chloro-2-phenylimidazol-5-yl]ethylene was refluxed in 2 ml each of glacial acetic acid and concentrated hydrochloric acid for 2 hours. The reaction mixture was concentrated to dryness under reduced pressure and the resulting residue was recrystalyzed from 5 ml of 60% ethanol to give 0.2 g of 1-(4-chlorobenzyl)-4-chloro-2-phenylimidazole-5-acetic acid as colorless needles. m.p. 203°–205° C. (decomp.).

EXAMPLE 67

3.8 g of 4-chloro-1-(3-methyl-4-methoxybenzyl)-2-phenylimidazole-5-acetic acid was dissolved in 10.8 ml of 1 N-sodium hydroxide under heating and the solution was concentrated to dryness under reduced pressure. The resulting residue was dissolved in 20 ml of acetone and triturated with ether to precipitate 4 g of sodium salt of the above-mentioned compound as colorless needles. m.p. 272°–274° C. (decomp.).

| Elementary analysis, for C20H18N2O3ClNa | | |
|---|---|---|
| | C (%) | H (%) | N (%) |
| Calcd. | 61.15 | 4.62 | 7.13 |
| Found | 60.87 | 4.84 | 7.25 |

EXAMPLE 68–74

There were obtained the following compounds in accordance with the procedures of Examples 1–67.

TABLE 3-II

| Example No. | R¹ | X¹ | X² | X³ | m.p. (° C.) |
|---|---|---|---|---|---|
| 68 |  | 2-C2H5O | H | H | 188–189 |
| 69 |  | 4-C2H5O | 3-CH3 | H | 188–189 |
| 70 | n-C4H9— | 4-CH3O | 3-CH3 | H | 142–143 |
| 71 | n-C4H9— | 2-C2H5O | H | H | 160–162 |
| 72 | n-C6H13— | 4-n-C4H9O | H | H | 137–139 |
| 73 | n-C6H13— | 4-CH3O | 3-CH3 | H | 98–101 (ammonium salt) |
| 74 | 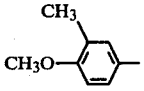 | 4-CH3O | 3-CH3 | H | 220–222 |

In accordance with the procedures of Examples 1 through 74, the following compounds can be synthesized:

2-Butyl-4-chloro-1-(2-methoxybenzyl)imidazole-5-acetic acid;

2-Isobutyl-4-chloro-1-(2-chlorobenzyl)imidazole-5-acetic acid;

2-Butyl-4-chloro-1-(2-ethoxybenzyl)imidazole-5-acetic acid;

2-Butyl-4-chloro-1-(2-propoxybenzyl)imidazole-5-acetic acid;

2-Butyl-4-chloro-1-(2-butoxybenzyl)imidazole-5-acetic acid;

2-Butyl-4-chloro-1-(2-bromobenzyl)imidazole-5-acetic acid; and

2-Phenyl-4-bromo-1-(2-methoxybenzyl)imidazole-5-acetic acid.

EXAMPLE 75

In cases in which the compound (I) of the present invention is employed as a treatment agent for essential hypertension, for example, it is utilized by the following formulation:

| 1. Tablets | |
|---|---|
| (1) 1-Benzyl-2-n-butyl-4-chloroimidazole-5-acetic acid, | 10 mg |
| (2) Lactose, | 35 mg |
| (3) Corn starch, | 150 mg |
| (4) Microcrystalline cellulose | 30 mg |
| (5) Magnesium stearate | 5 mg |
| One tablet | 230 mg |

(1), (2), (3) and two thirds of (4) were mixed with a half of (5) and granulated. The remainders of (4) and (5) were added to the granules and pressed into a tablet.

| 2. Capsules | |
|---|---|
| (1) 1-(4-Ethoxybenzyl)-2-phenyl-5-chloroimidazole-5-acetic acid, | 10 mg |
| (2) Lactose | 90 mg |
| (3) Microcrystalline cellulose | 70 mg |
| (4) Magnesium stearate | 10 mg |
| One capsule | 190 mg |

(1), (2) and (3) were mixed with one fourth of (4), and granulated. The remainder of (4) was added to the granules and the mixture was filled into a gelatin capsule.

| 3. Injections | |
|---|---|
| (1) Sodium 1-(4-methylbenzyl)-2-phenyl-5-chloro-imidazole-5-acetate | 10 mg |
| (2) Inosite | 100 mg |
| (3) Benzyl alcohol | 20 mg |
| One ampoule | 130 mg |

(1), (2) and (3) were dissolved in distilled water for injection to make 2 ml of the solution, and filled into an ampoule. The whole preparation process was conducted in the sterile condition.

REFERENCE EXAMPLE 1

5.2 g of 2-phenyl-5-hydroxymethylimidazole and 4.43 g of N-chlorosuccinimide were stirred in a mixture of 40 ml of methyl cellosolve and 60 ml of dioxane at 50° C. for 8 hours. 50 ml of ether was added to the reaction solution, and the crystals separated out were recrystallized from 100 ml of ethanol, resulting in 4.6 g of 2-phenyl-4-chloro-5-hydroxymethylimidazole as colorless, prism-formed crystals, m.p. 190°–195° C. (decomp.).

| | Elementary analysis, for $C_{10}H_9N_2OCl$ | | | |
|---|---|---|---|---|
| | C (%) | H (%) | N (%) | Cl (%) |
| Calcd. | 57.52 | 4.35 | 13.42 | 16.98 |
| Found | 57.89 | 4.30 | 13.39 | 16.98 |

REFERENCE EXAMPLES 2 to 9

In accordance with the procedure of Reference Example 1, there were obtained the following compounds.

TABLE 4

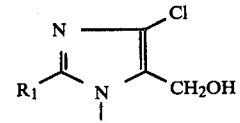

| Reference Example No. | $R^1$ | m.p. (° C.) |
|---|---|---|
| 2 | n-$C_4H_9$— | 147–148 |
| 3 | n-$C_4H_9O$—  | 190–191 |
| 4 | $CH_3$— 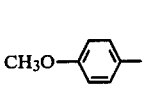 | 209–211 |
| 5 | $CH_3O$— 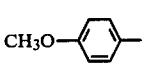 | 191–193 |
| 6 | Cl— 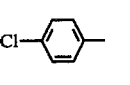 | 209–211 |
| 7 | t-$C_4H_9$— | 170–174 |
| 8 | n-$C_3H_7$— | 172–175 |
| 9 |  | 185–186 |

REFERENCE EXAMPLE 10

1 g of 2-phenyl-4-chloro-5-hydroxymethylimidazole, together with 0.7 ml of p-methylbenzyl bromide and 3 g of potassium carbonate, was stirred in 10 ml of dimethylformamide at 30° C. for 2 days. The reaction solution was poured into 100 ml of water, and the precipitate deposited was chromatographed on a column of 30 g of silica gel, followed by eluting with chloroform. The initially eluted fraction was collected, and recrystallization from aqueous methanol yielded 0.5 g of 2-phenyl-4-chloro-5-hydroxymethyl-1-(4-methylbenzyl)imidazole as colorless, needle-formed crystals, m.p. 173°–175° C.

REFERENCE EXAMPLE 11

0.7 g of sodium was dissolved in 15 ml of methanol, and the solution was combined with 30 ml of a methanol solution of 5.6 g of 2-cyclopentyl-4-chloro-5-hydroxymethylimidazole. The mixed solution was evaporated to dryness under reduced pressure, and the residue was dissolved in 20 ml of dimethylformamide, followed by adding 3.9 g of benzyl chloride to stir at 40° to 45° C. for 3 hours. The reaction solution was poured into 300 ml of water to extract with two 100 ml portions of ethyl acetate. The ethyl acetate layer was evaporated to dryness under reduced pressure, and the residue was chromatographed on a column of 200 g of silica gel to elute with ethyl acetate-benzene (1:3). The initially eluted fraction was collected to evaporate to dryness under reduced pressure. The residue was dissolved in ether, whereby there separated out crystals. Addition of petroleum ether, followed by recovery by filtration, yielded 2 g of 2-cyclopentyl-4-chloro-5-hydroxymethyl-1-benzylimidazole as slightly yellow, prism-formed crystals, m.p. 102°–103° C.

| Elementary analysis, for $C_{16}H_{19}N_2OCl$ | | | |
|---|---|---|---|
| | C (%) | H (%) | N (%) |
| Calcd. | 66.09 | 6.59 | 9.63 |
| Found | 66.37 | 6.55 | 9.59 |

REFERENCE EXAMPLE 12

5.8 g of 1-benzyl-2-cyclohexyl-5-hydroxymethylimidazole, together with 3.2 g of N-chlorosuccnimide, was stirred in 58 ml of methyl cellosolve at 40° C. for 1 hour. The reaction solution was poured into 500 ml of water and extract with two portions of 200 ml of ether. The ether layer was evaporated to dryness under reduced pressure, and the residue was chromatographed on a column of 200 g of silica gel to elute with ethyl acetate-benzene (1:4). The objective fractions were collected and evaporated to dryness under reduced pressure. Recrystallization of the residue from ether yielded 1.6 g of 1-benzyl-4-chloro-2-cyclohexyl-5-hydroxymethylimidazole as colorless, needle-formed crystals, m.p. 160°–161° C.

| Elementary Analysis, for $C_{17}H_{21}N_2OCl$ | | | |
|---|---|---|---|
| | C (%) | H (%) | N (%) |
| Calcd. | 66.99 | 6.95 | 9.19 |
| Found | 66.90 | 6.87 | 9.25 |

REFERENCE EXAMPLES 13 to 23

In accordance with the procedures of Reference Examples 10, 11 and 12, there were obtained the following compounds:

TABLE 5

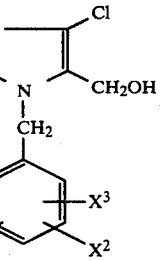

| Reference Example No. | $R^1$ | $X^1$ | $X^2$ | $X^3$ | m.p. (° C.) |
|---|---|---|---|---|---|
| 13 | t-$C_4H_9$ | H | H | H | 160–163 |
| 14 | n-$C_3H_7$ | H | H | H | 105–106 |
| 15 | n-$C_4H_9$ | H | H | H | 65–67 |
| 16 | n-$C_4H_9$ | 2-Cl | H | H | 101–103 |
| 17 | n-$C_4H_9$ | 2-$NO_2$ | H | H | 107–108 |
| 18 | i-$C_3H_7$ | H | H | H | 80–82 |
| 19 | n-$C_5H_{11}$ | H | H | H | 69–70 |
| 20 | $CH_3$ | H | H | H | 167–168 |
| 21 | $C_2H_5$ | H | H | H | 95–97 |
| 22 | n-$C_5H_{11}$ | 2-Cl | H | H | 112–114 |
| 23 | n-$C_6H_{13}$ | 2-Cl | H | H | 96–98 |

REFERENCE EXAMPLE 24

In 50 ml of tetrahydrofuran was dissolved 2.1 g of 1-benzyl-2-(4-n-butyrylaminophenyl)-4-chloro-5-hydroxymethylimidazole. 300 mg of lithium aluminium hydride was added to the solution, followed by boiling for 4 hours. The procedure was repeated twice. 1 ml of water and 1.8 ml of 6 N-hydrochloric acid were added to the reaction solution, which was shaken well, and insolubles were filtered out. The filtrate was evaporated to dryness under reduced pressure, and the residue was dissolved in 20 ml of methanol to add water little by little. There was obtained 1.5 g of 1-benzyl-2-(4-n-butylaminopheyl)-4-chloro-5-hydroxymethylimidazole separated out as colorless needle-formed crystals, m.p. 161°–163° C.

| Elementary analysis, for $C_{21}H_{24}N_3OCl$ | | | | |
|---|---|---|---|---|
| | C (%) | H (%) | N (%) | Cl (%) |
| Calcd. | 68.75 | 6.59 | 11.44 | 9.67 |
| Found | 68.45 | 6.59 | 11.26 | 9.32 |

REFERENCE EXAMPLE 25

10 g of 4-chloro-5-formyl-2-phenylimidazole was added little by little to a mixture of 25 ml each of fuming nitric acid (specific gravity of 1.52) and concentrated sulfuric acid. After addition was completed, the mixture was stirred at room temperature for 1 hour, and poured into 400 ml of ice-water. Recrystallization of the resultant precipitate from 100 ml of dimethylformamide yielded 9 g of 4-chloro-5-formyl-2-(4-nitrophenyl)imidazole as slightly yellow, needle-formed crystals, m.p. of not lower than 300° C.

| Elementary analysis, for $C_{10}H_6N_3O_3Cl$ | | | | |
|---|---|---|---|---|
| | C (%) | H (%) | N (%) | Cl (%) |
| Calcd. | 47.73 | 2.40 | 16.70 | 14.08 |
| Found | 47.44 | 2.57 | 16.90 | 13.91 |

REFERENCE EXAMPLE 26

In 35 ml of glacial acetic acid was dissolved 3.5 g of 1-benzyl-4-chloro-5-cyanomethyl-2-(4-dimethylaminophenyl)imidazole, and 1 ml of fuming nitric acid (specific gravity of 1.52) was added dropwise to the solution under cooling with water. The mixture was stirred at room temperature for 1 hour and poured into 500 ml of ice-water. The resultant precipitate was chromatographed on a column of 60 g of silica gel, followed by eluting with chloroform. The objective fractions were collected and concentrated to about 5 ml. Addition of 10 ml of ethanol yielded 1.7 g of 1-benzyl-4-chloro-5-cyanomethyl-2-(4-dimethylamino-3,5-dinitrophenyl)imidazole as yellow prism-formed crystals, m.p. 173°–175° C.

| Elementary analysis, for $C_{20}H_{17}N_6O_4Cl$ | | | | |
|---|---|---|---|---|
| | C (%) | H (%) | N (%) | Cl (%) |
| Calcd. | 54.45 | 3.89 | 19.04 | 8.05 |
| Found | 54.17 | 3.87 | 19.31 | 8.25 |

REFERENCE EXAMPLE 27

2 g of 1-benzyl-4-chloro-5-cyanomethyl-2-(4-dimethylaminophenyl)imidazole and 1 g of N-chlorosuccinimide were stirred in 30 ml of dioxane at 50° C. for 2 hours. The reaction solution was evaporated to dryness under reduced pressure, and the residue was dissolved in 100 ml of chloroform, followed by washing twice with water and evaporating to dryness under reduced pressure. The residue was recrystallized twice from 20 ml of methanol, thus yielding 1.4 g of 1-benzyl-4-chloro-5-cyanomethyl-2-(4-dimethylamino-3-chlorophenyl)imidazole as slightly yellow, needle-formed crystals, m.p. 142°–143° C.

| | Elementary analysis, for $C_{20}H_{19}N_3O_2Cl_2$ | | | |
|---|---|---|---|---|
| | C (%) | H (%) | N (%) | Cl (%) |
| Calcd. | 59.42 | 4.73 | 10.38 | 17.54 |
| Found | 59.64 | 4.61 | 10.37 | 17.43 |

REFERENCE EXAMPLE 28

In 40 ml of chloroform was suspended 8.2 g of 1-benzyl-4-chloro-2-(4-nitrophenyl)-5-hydroxymethylimidazole, and 3.7 ml of thionyl chloride was added dropwise to the suspension. After allowing it to stand at room temperature for 2 hours, the reaction solution was evaporated to dryness under reduced pressure. 50 ml of toluene was added to the residue, followed by evaporating to dryness under reduced pressure again. The residue was dissolved in 80 ml of chloroform and cooled with ice. 7 g of sodium cyanide and 0.8 g of tetrabutyl ammonium bromide were dissolved in 25 ml of ice water, and the solution was added to the chloroform solution mentioned above, followed by stirring vigorously at 0° C. for 2 hours and further at room temperature for 5 hours. The chloroform layer was washed with 50 ml of water, and chromatographed on a column of 80 g of silica gel, followed by eluting with chloroform. The fractions of the objective compound were collected and evaporated to dryness under reduced pressure, followed by dissolving the residue in 50 ml of methanol to allow to cool. There was obtained 7 g of 1-benzyl-4-chloro-2-(4-nitrophenyl)-5-cyanomethylimidazole resulted as slightly yellow, needle-formed crystals, m.p. 125°–128° C.

| | Elementary analysis, for $C_{18}H_{13}N_4O_2Cl$ | | | |
|---|---|---|---|---|
| | C (%) | H (%) | N (%) | Cl (%) |
| Calcd. | 61.29 | 3.71 | 15.87 | 10.05 |
| Found | 61.14 | 3.65 | 15.74 | 9.95 |

REFERENCE EXAMPLE 29

In 18 ml of chloroform was dissolved 1.8 g of 1-benzyl-4-chloro-2-cyclopentyl-5-hydroxymethylimidazole, and 2.2 ml of thionyl chloride was added dropwise to the solution, followed by stirring at room temperature for 1 hour. The reaction solution was evaporated to dryness under reduced pressure, and 20 ml of benzene was added to the residue to distill off the solvent. The procedure was repeated twice. The residue was dissolved in 10 ml of dimethylsulfoxide, and the solution was added dropwise to a suspension of 1.8 g of dried sodium cyanide in 10 ml of dimethylsulfoxide at room temperature with stirring. After addition was completed, the solution was vigorously stirred at room temperature for 1 hour, followed by pouring into 200 ml of water to extract with two 100 ml portions of ethyl acetate. The ethyl acetate layer was evaporated to dryness under reduced pressure, and the residue was chromatographed on a column of 70 g of silica gel, followed by eluting with benzene-acetone (20:1). The fractions of the objective compound were collected and evaporated to dryness under reduced pressure. The residue was dissolved in 50 ml of ether, and 1.5 ml of 20% hydrogen chloride-ethanol was added to the solution. There was obtained 1.5 g of 1-benzyl-4-chloro-2-cyclopentyl-5-cyanomethylimidazole hydrochloride deposited as colorless, plate-formed crystals, m.p. 124°–132° C.

| | Elementary analysis, for $C_{17}H_{18}N_3Cl\cdot HCl$ | | |
|---|---|---|---|
| | C (%) | H (%) | N (%) |
| Calcd. | 60.72 | 5.69 | 12.50 |
| Found | 60.67 | 5.70 | 12.35 |

REFERENCE EXAMPLES 30 to 65

In accordance with the procedures of Reference Examples 28 and 29, there were obtained the following compounds:

TABLE 6

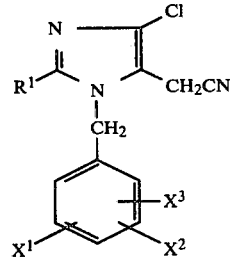

| Reference Example No. | $R^1$ | $X^1$ | $X^2$ | $X^3$ | m.p. (°C.) |
|---|---|---|---|---|---|
| 30 | ⌬— | 2-Cl | H | 5-NO₂ | 150–151 |
| 31 | ⌬— | 4-CH₂ | H | H | 146–148 |

TABLE 6-continued
| Reference Example No. | R¹ | X¹ | X² | X³ | m.p. (°C.) |
|---|---|---|---|---|---|
| 32 | phenyl | 2-CH₃O | H | H | 112–113 |
| 33 | phenyl | 3-CH₃O | H | H | 65–70 |
| 34 | phenyl | 4-CH₃O | H | H | 89–90 |
| 35 | phenyl | 4-C₂H₅O | H | H | 108–110 |
| 36 | phenyl | 4-n-C₄H₉O | H | H | 80–81 |
| 37 | phenyl | 4-C₆H₅CH₂O | H | H | 152–155 |
| 38 | phenyl | 3-CH₃O | H | 4-CH₃O | 113–114 |
| 39 | phenyl | 3-CH₃ | H | 4-CH₃O | 137–138 |
| 40 | phenyl | 3-CH₃O | 4-CH₃O | 5-CH₃O | 124–125 |
| 41 | phenyl | 4-Cl | H | H | 155–156 |
| 42 | phenyl | 2-Cl | H | H | 163–164 |
| 43 | phenyl | 2-Cl | 4-Cl | H | 172–173 |
| 44 | phenyl | 2-Cl | 6-Cl | H | 189–190 |
| 45 | phenyl | 2-Br | H | H | 153 |
| 46 | 2-NO₂-phenyl | H | H | H | 157–159 |

TABLE 6-continued

Structure:
$R^1$-C(=N)-N(-CH$_2$-Ar)-C(Cl)=C(-CH$_2$CN)
where Ar is phenyl substituted with $X^1$, $X^2$, $X^3$

| Reference Example No. | $R^1$ | $X^1$ | $X^2$ | $X^3$ | m.p. (°C.) |
|---|---|---|---|---|---|
| 47 | 3,4,5-(CH$_3$O)$_3$-C$_6$H$_2$- | H | H | H | 100–101 |
| 48 | 3,4-(CH$_3$O)$_2$-C$_6$H$_3$- | H | H | H | 147–149 |
| 49 | 3-CH$_3$-4-CH$_3$O-C$_6$H$_3$- | H | H | H | 110–112 |
| 50 | 3-CH$_3$O-4-C$_6$H$_5$CH$_2$O-C$_6$H$_3$- | H | H | H | 94–96 |
| 51 | CH$_3$ | H | H | H | 114–115 |
| 52 | C$_2$H$_5$ | H | H | H | 70–71 |
| 53 | i-C$_3$H$_7$ | H | H | H | 130–131 |
| 54 | n-C$_4$H$_9$ | H | H | H | 122–123 (hydrochloride) |
| 55 | n-C$_4$H$_9$ | 2-Cl | H | H | 117–118 (hydrochloride) |
| 56 | n-C$_4$H$_9$ | 2-NO$_2$ | H | H | 82–84 |
| 57 | n-C$_3$H$_7$ | H | H | H | 129–133 (hydrochloride) |
| 58 | t-C$_4$H$_9$ | H | H | H | 140–145 (hydrochloride) |
| 59 | n-C$_5$H$_{11}$ | H | H | H | 120–123 (hydrochloride) |
| 60 | n-C$_5$H$_{11}$ | 2-Cl | H | H | 118–120 |
| 61 | n-C$_6$H$_{13}$ | 2-Cl | H | H | 126–128 |
| 62 | cyclohexyl- | H | H | H | 117–118 |
| 63 | 4-(n-C$_3$H$_7$CONH)-C$_6$H$_4$- | H | H | H | 152–154 |
| 64 | 3,5-Cl$_2$-4-CH$_3$O-C$_6$H$_2$- | H | H | H | 188–190 |
| 65 | n-C$_4$H$_9$ | 4-n-C$_4$H$_9$O | H | H | 120–122 (hydrochloride) |
| 66 | C$_6$H$_5$- | 2-C$_2$H$_5$O | H | H | 110–112 |
| 67 | C$_6$H$_5$- | 4-C$_2$H$_5$O | 3-CH$_3$ | H | 117–119 |
| 68 | n-C$_4$H$_9$- | 4-CH$_3$O | 3-CH$_3$ | H | oil IR(Nujol):2240cm (CN) |

TABLE 6-continued

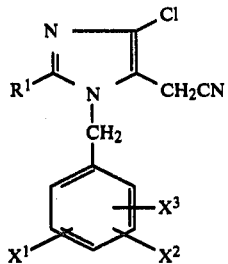

| Reference Example No. | $R^1$ | $X^1$ | $X^2$ | $X^3$ | m.p. (°C.) |
|---|---|---|---|---|---|
| 69 | n-$C_4H_9$— | 2-$C_2H_5O$ | H | H | oil IR(Nujol):2240cm (CN) |
| 70 | n-$C_6H_{13}$— | 4-n-$C_4H_9O$ | H | H | 105–110 (hydrochloride) |
| 71 | n-$C_6H_{13}$— | 4-$CH_3O$ | 3-$CH_3$ | H | 126–127 (hydrochloride) |
| 72 | 2-CH₃,4-CH₃O-phenyl | 4-$CH_3O$ | 3-$CH_3$ | H | 85–90 |

EXPERIMENT EXAMPLE 1

Antagonistic effect of the compound (I) of the present invention on angiotensin II (hereinafter referred to briefly as "A II") (with aortic blood vessel of rabbits)

The blood-vessel preparation and reaction were done in accordance with the method as described in "European Journal of Pharmacology", 18, 316 (1972). While employing A II in the concentration of $4 \times 10^{-9}$ M, the potency of inhibition was calculated by the following equation from changes in isometric tension of the blood vessel brought about by A II and that found after treatment with a test drug substance for 15 minutes, respectively.

$$\text{Potency of inhibition (\%)} = \frac{T_1 - T_2}{T_1} \times 100$$

where;
$T_1$ = Change in isometric tension of the blood vessel brought about by A II without a test drug substance (g)
$T_2$ = Change in tension found after treatment with a test drug substance (g)

The results are shown in Table 7.

TABLE 7

| Compound | | | | Concn. of drug | |
|---|---|---|---|---|---|
| $R^1$ | $X^1$ | $X^2$ | $X^3$ | substance (M) | Inhibition (%) |
| phenyl | 4-$CH_3$ | H | H | $10^{-5}$ | 80 |
| phenyl | 2-$CH_3$ | H | H | $10^{-5}$ | 58 |
| phenyl | 4-Cl | H | H | $10^{-5}$ | 25 |
| phenyl | 2-Cl | H | H | $10^{-5}$ | 90 |

TABLE 7-continued
| | Compound | | | Concn. of drug | |
|---|---|---|---|---|---|
| $R^1$ | $X^1$ | $X^2$ | $X^3$ | substance (M) | Inhibition (%) |
|  | 2-Cl | 4-Cl | H | $10^{-5}$ | 30 |
|  | 2-Cl | H | 6-Cl | $10^{-6}$ | 34 |
|  | 2-Cl | H | 6-F | $10^{-6}$ | 64 |
|  | 2-Cl | 5-$NO_2$ | H | $10^{-6}$ | 34 |
|  | 2-Br | H | H | $10^{-6}$ | 60 |
|  | 2-F | H | H | $10^{-6}$ | 23 |
|  | H | H | H | $10^{-5}$ | 63 |
|  | H | H | H | $10^{-5}$ | 35 |
|  | H | H | H | $10^{-5}$ | 50 |
|  | H | H | H | $10^{-5}$ | 30 |
|  | H | H | H | $10^{-5}$ | 32 |
|  | H | H | H | $10^{-5}$ | 18 |
|  | H | H | H | $10^{-5}$ | 51 |
|  | H | H | H | $10^{-5}$ | 73 |

TABLE 7-continued

Structure:

$$\text{R}^1\text{-imidazole with N-CH}_2\text{-phenyl(X}^1\text{,X}^2\text{,X}^3\text{), Cl and CH}_2\text{CO}_2\text{H substituents}$$

| Compound R¹ | X¹ | X² | X³ | Concn. of drug substance (M) | Inhibition (%) |
|---|---|---|---|---|---|
| 2,6-dinitro-4-(dimethylamino)phenyl [(CH₃)₂N, 2×O₂N] | H | H | H | $10^{-5}$ | 86 |
| 2-chloro-3,5-dinitrophenyl (Cl, 2×O₂N) | H | H | H | $10^{-6}$ | 82 |
| 3-chloro-4-(diethylamino)phenyl [(C₂H₅)₂N, Cl] | H | H | H | $10^{-6}$ | 25 |
| 2-hydroxyphenyl (OH) | H | H | H | $10^{-5}$ | 55 |
| 3-chloro-4-(dimethylamino)phenyl [(CH₃)₂N, Cl] | H | H | H | $10^{-6}$ | 33 |
| 3-bromo-4-(dimethylamino)phenyl [(CH₃)₂N, Br] | H | H | H | $10^{-6}$ | 18 |
| 3,4-dihydroxyphenyl (HO, HO) | H | H | H | $10^{-6}$ | 34 |
| 3-methoxyphenyl (CH₃O) | 2-Cl | H | H | $10^{-6}$ | 23 |
| 3-hydroxy-4-methoxyphenyl (HO, CH₃O) | H | H | H | $10^{-6}$ | 16 |
| phenyl | 2-CH₃O | H | H | $10^{-6}$ | 42 |
| phenyl | 3-CH₃O | H | H | $10^{-5}$ | 73 |
| phenyl | 4-CH₃O | H | H | $10^{-5}$ | 61 |
| phenyl | 4-C₂H₅O | H | H | $10^{-6}$ | 43 |

TABLE 7-continued

| | Compound | | | Concn. of drug | |
|---|---|---|---|---|---|
| $R^1$ | $X^1$ | $X^2$ | $X^3$ | substance (M) | Inhibition (%) |
| phenyl | 2-$C_2H_5O$ | H | H | $10^{-6}$ | 41 |
| phenyl | 4-$C_4H_9O$ | H | H | $10^{-6}$ | 56 |
| phenyl | 4-$C_6H_5CH_2O$ | H | H | $10^{-5}$ | 19 |
| phenyl | 3-$CH_3O$ | H | 4-$CH_3O$ | $10^{-6}$ | 38 |
| phenyl | 3-$CH_3$ | H | 4-$CH_3O$ | $10^{-6}$ | 80 |
| phenyl | 3-$CH_3$ | H | 4-$C_2H_5O$ | $10^{-6}$ | 81 |
| 3,4-di-$CH_3O$-phenyl | H | H | H | $10^{-6}$ | 18 |
| 3-$CH_3$-4-$CH_3O$-phenyl | H | H | H | $10^{-6}$ | 32 |
| 3-$CH_3$-4-$CH_3O$-phenyl | 3-$CH_3$ | 4-$CH_3O$ | H | $10^{-6}$ | 54 |
| 3-$CH_3O$-4-$C_6H_5CH_2O$-phenyl | H | H | H | $10^{-6}$ | 18 |
| $CH_3$— | H | H | H | $10^{-5}$ | 38 |
| $C_2H_5$— | H | H | H | $10^{-6}$ | 36 |
| i-$C_3H_7$— | H | H | H | $10^{-6}$ | 41 |
| n-$C_4H_9$— | H | H | H | $10^{-6}$ | 55 |
| n-$C_4H_9$— | 2-Cl | H | H | $10^{-7}$ | 75 |
| n-$C_4H_9$— | 2-$NO_2$ | H | H | $10^{-8}$ | 30 |
| n-$C_4H_9$— | 3-$CH_3$ | 4-$CH_3O$ | H | $10^{-6}$ | 99 |
| n-$C_4H_9$— | 2-$C_2H_5O$ | H | H | $10^{-6}$ | 53 |
| n-$C_3H_7$— | H | H | H | $10^{-6}$ | 22 |
| t-$C_4H_9$— | H | H | H | $10^{-6}$ | 10 |
| n-$C_5H_{11}$— | H | H | H | $10^{-6}$ | 65 |
| n-$C_5H_{11}$— | 2-Cl | H | H | $10^{-7}$ | 57 |
| n-$C_6H_{13}$— | 2-Cl | H | H | $10^{-7}$ | 84 |
| n-$C_6H_{13}$— | 4-n-$C_4H_9O$ | H | H | $10^{-6}$ | 100 |
| n-$C_6H_{13}$ | 3-$CH_3$ | 4-$CH_3O$ | H | $10^{-6}$ | 100 |
| cyclopentyl | H | H | H | $10^{-6}$ | 34 |

TABLE 7-continued

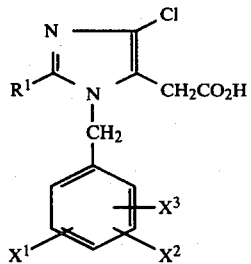

| Compound | | | | Concn. of drug | |
|---|---|---|---|---|---|
| $R^1$ | $X^1$ | $X^2$ | $X^3$ | substance (M) | Inhibition (%) |
| C6H11— | H | H | H | $10^{-6}$ | 18 |
| n-C4H9— | 4-n-C4H9O | H | H | $10^{-6}$ | 85 |

EXPERIMENT EXAMPLE 2

Inhibitory activity of the compound (I) of the present invention against angiotensin II-induced elevation of blood pressure in rats Male SD rats weighing 250 to 350 g, under anesthesia with pentobarbital sodium (50 mg/kg, intraperitoneally), were operated on for cannulation in trachea, carotid and femoral arteries. In order to maintain the anesthesia, pentobarbital dissolved in physiological saline was administered to the rats by continuous intravevous infusion (350 og/kg/min.). About one hour after operation, when the blood pressure got stable, A II was given by continuous intravenous infusion at a rate of 20 ng/kg/min. 30 to 60 minutes later, the stable blood pressure was realized. The elevation of blood pressure after the infusion of A II, as compared with the one before the infusion, was 45.5±2.1 mmHg (for 75 cases).

Then, a test drug substance (dissolved in 500 μl physiological saline/100 g body weight) was administered intravenously to take measurements of blood pressure after 10, 30 and 90 minutes. The potency of inhibition by a drug substance was calculated by the following equation:

$$\text{Potency of inhibition (\%)} = \frac{Pf}{Pe} \times 100$$

where;

Pf=Fall in blood pressure after administration of a drug substance (mmHg)

Pe=Elevation of blood pressure due to A II (mmHg)

The results are shown in Table 8.

TABLE 8

| Compound | | | | Doses | | Inhibition (%), after; | | |
|---|---|---|---|---|---|---|---|---|
| $R^1$ | $X^1$ | $X^2$ | $X^3$ | (mg/kg) | Cases | 10 min. | 30 min. | 90 min. |
| HO—C6H4— | H | H | H | 0.3 | 3 | 10.7 ± 1.8 | 24.3 ± 2.3 | 11.7 ± 6.0 |
|  |  |  |  | 0.5 | 4 | 14.8 ± 1.8 | 36.0 ± 3.0 | 35.0 ± 3.9 |
| H2N—C6H4— | H | H | H | 0.5 | 3 | 17.7 ± 1.2 | 45.3 ± 2.4 | 37.0 ± 8.6 |
| C6H5— | 2-Cl | H | H | 1.0 | 4 | 11.8 ± 1.8 | 36.5 ± 4.5 | 32.3 ± 7.0 |
| n-C4H9 | H | H | H | 0.1 | 3 | 19.6 ± 1.5 | 64.3 ± 15.3 | 60.0 ± 21.5 |
|  |  |  |  | 0.3 | 1 | 25 | 94 | 94 |
| O2N,Cl,O2N—C6H2— | H | H | H | 0.1 | 4 | 22.5 ± 3.2 | 55 ± 7.5 | 55 ± 7.5 |
|  |  |  |  | 0.3 | 2 | 18 | 72 | 72 |
| C6H5— | 4-n-C4H9O | H | H | 3.0 | 1 | 20 | 40 | 0 |
|  |  |  |  | 0.03 | 2 | 17 | 46.5 | 40 |
| n-C4H9 | 2-Cl | H | H | 0.1 | 1 | 38 | 100 | 86 |
| C6H5— | 3-CH3 | 4-CH3O | H | 0.5 | 4 | 33 ± 15 | 60 ± 18 | 62 ± 7 |

What is claimed is:

1. A compound of the formula:

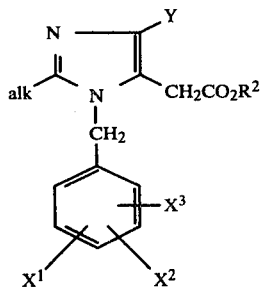

wherein alk is lower alkyl or lower cycloalkyl; each of $X^1$, $X^2$ and $X^3$ is independently hydrogen, halogen, nitro, amino, lower alkyl, lower alkoxyl, benzyloxyl or hydroxyl; Y is halogen and $R^2$ is hydrogen or lower alkyl, or a pharmaceutically acceptable salt thereof.

2. A compound according to claim 1, wherein Y is chlorine.

3. A compound according to claim 1, wherein $R^2$ is hydrogen.

4. A compound according to claim 1, which is 1-(2-chlorobenzyl)-2-n-butyl-4-chloroimidazole-5-acetic acid.

5. A compound of the formula:

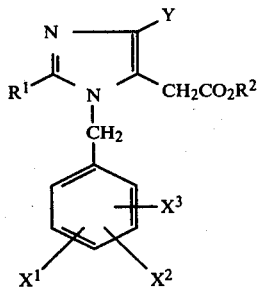

wherein $R^1$ is phenyl which is substituted with only one nitro, amino, monobutylamino or hydroxyl, or with two or three of halogen, nitro, amino, mono(lower alkyl)amino, di(lower alkyl)amino, lower alkyl, lower alkoxyl, benzyloxyl or/and hydroxyl groups; each of $X^1$, $X^2$ and $X^3$ is independently hydrogen, halogen, nitro, amino, lower alkyl, lower alkoxyl, benzyloxyl or hydroxyl; Y is halogen and $R^2$ is hydrogen or lower alkyl, or a pharmaceutically acceptable salt thereof.

6. A compound according to claim 5, wherein $R^1$ is phenyl substituted with two to three of halogen, mono(lower alkyl)amino, di(lower alkyl)amino, lower alkyl, lower alkoxyl, benzyloxyl or/and hydroxyl, and $X^1$, $X^2$ and $X^3$ are each hydrogen.

7. A compound according to claim 5, wherein Y is chlorine.

8. A compound according to claim 5, wherein $R^2$ is hydrogen.

9. A compound according to claim 5, which is 1-benzyl-4-chloro-2-(4-chloro-3,5-dinitrophenyl)imidazole-5-acetic acid.

10. A compound of the formula:

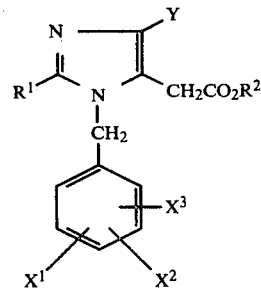

wherein
$R^1$ is unsubstituted phenyl or phenyl substituted only with one halogen, di(lower alkyl)amino, lower alkyl or lower alkoxyl;
$X^1$ is halogen, lower alkyl, lower alkoxyl, benzyloxyl or hydroxyl, and each of $X^2$ and $X^3$ is independently hydrogen, halogen, nitro, amino, lower alkyl, lower alkoxyl, benzyloxyl or hydroxyl;
Y is halogen and
$R^2$ is hydrogen or lower alkyl
or a pharmaceutically acceptable salt thereof.

11. A compound according to claim 10, wherein $R^1$ is unsubstituted phenyl, and $X^1$ is $C_{1-4}$ alkyl, $X_2$ is $C_{1-4}$ alkoxyl and $X_3$ is hydrogen.

12. A compound according to claim 10, wherein Y is chlorine.

13. A compound according to claim 10, wherein $R^2$ is hydrogen.

14. A compound according to claim 10, which is 4-chloro-1-(4-methoxy-3-methylbenzyl)-2-phenylimidazole-5-acetic acid.

15. A compound according to claim 10, which is 4-chloro-1-(4-ethoxy-3-methylbenzyl)-2-phenylimidazole-5-acetic acid.

16. A pharmaceutical composition which contains an amount effective for producing hypotensive activity in a mammal of a compound of claim 2, 6, 11, 1-15 or 3, and a pharmaceutically acceptable carrier, vehicle or diluent therefor.

17. A method for producing hypotensive activity in a mammal, which comprises administering to said mammal a hypotensively effective amount of a compound of claim 2, 6, 11, 1-15 or 3.

* * * * *